United States Patent [19]

Takebe et al.

[11] 4,084,591

[45] Apr. 18, 1978

[54] WATER DISPERSIBLE ABSORBER FOR BLOOD AND THE LIKE

[75] Inventors: Toshio Takebe, Ohmiya; Takashi Yamazaki, Ohtsu, both of Japan

[73] Assignee: Eisai Co., Ltd., Japan

[21] Appl. No.: 657,264

[22] Filed: Feb. 11, 1976

[30] Foreign Application Priority Data

Feb. 14, 1975 Japan .................................. 50-17969

[51] Int. Cl.$^2$ ............................................. A61F 13/20
[52] U.S. Cl. .............................. 128/285; 128/290 R; 536/91; 536/95; 536/96; 536/99; 536/100
[58] Field of Search ............. 128/285, 290 R; 536/91, 536/95, 96, 99, 100

[56] References Cited

U.S. PATENT DOCUMENTS

| 1,505,043 | 8/1924 | Lilienfeld | 536/100 |
|---|---|---|---|
| 3,029,817 | 4/1962 | Harwood et al. | 128/290 R |
| 3,251,824 | 5/1966 | Battista | 536/100 |
| 3,278,520 | 10/1966 | Klug | 536/95 |
| 3,388,082 | 6/1968 | Rodgers et al. | 536/91 |
| 3,901,236 | 8/1975 | Assarsson et al. | 128/284 |
| 3,954,104 | 5/1976 | Kraskin et al. | 128/285 |

Primary Examiner—Ronald W. Griffin
Attorney, Agent, or Firm—Wenderoth, Lind & Ponack

[57] ABSTRACT

Novel absorber for the blood and the like, particularly a tampon for menses, which is made of the filaments of a lower alkyl or a lower hydroxyalkyl substituted cellulose ether. The absorber is insoluble in the blood and the like when it is used, but it is dispersible and soluble in water when it is thrown away.

8 Claims, No Drawings

WATER DISPERSIBLE ABSORBER FOR BLOOD AND THE LIKE

This invention relates to a water dispersible absorber for blood and the like. More particularly, this invention relates to a water dispersible cellulose ether absorber for blood and the like, which is, when thrown away in water, capable of being readily flushed without plugging or stopping the drain pipes, and then being gradually dispersed and dissolved in the storage water in the sewer pipes.

Recently, the use of vaginal tampons (hereinafter referred to as "tampons") for absorption of menses has been rapidly become popular. However, the tampon is often apt to be discarded in a flush toilet, because its volume is relatively smaller than that of sanitary pad (absorbent napkin or towel of patch type) even after absorption of the blood of menses. Since the conventional tampons on the market are made of absorbent cotton as raw materials, they often plug the drain pipe of the toilet when they are discarded after absorption of the blood. Further, after they have passed through the drainpipe, they tend to accumulate in the sewer pipe and sanitary wares or facilities, thereby causing various problems.

An object of this invention is therefore to provide a water dispersible absorber or absorptive material for blood and the like which is capable of being dispersed flush water and which may be discharged therefrom without plugging the drain pipe, and which is then gradually dispersed and dissolved in the sewage pipes after use.

Various known water-soluble fibers include filaments and staple fibers made by spinning polyvinylalcohol, polyethylene oxide or others. However, problems have been encountered in that these filaments and staple fibers which are made of such synthetic polymers can be scarcely decomposed by the action of bacteria and enzymes, whereby they cause various problems of environmental pollution in their treatment after the use. It is therefore considered that these absorbers made of synthetic polymers should not be broadly employed.

We have thoroughly studied the problem and found that a filament made of a certain cellulose ether is adapted for use as a water dispersible absorber for blood and the like. The term "the absorber for blood and the like" in the specification means cottonlike materials, gauze and bandage to be used for absorbing blood, lymph, humor, pus and the like which exude from the body or the organs due to wounds, surgical operations and blood of menses, and the like; and sanitary pads (absorptive napkin or towel of patch type), vaginal tampons (the compressed and moulded absorber of insertion type) and the like for treating the blood of menses. Among these absorbers, however, none are fully suitable for tampons due to severe conditions for selection of raw material therefor. This reason may be illustrated as follows.

The tampons are usually pressed to a compact form, and are inserted in vagina when they are used. After absorbing the blood of menses, they are pulled out with a string connected to the tampon and are then discarded. Therefore, they are required to be made of materials having the following physical properties e.g. having good properties for compression molding; being immediately expandable to their original volume by absorbing the blood of menses; not dissolving in vagina despite the absorption of the blood of menses; and maintaining the original form of tampon and rigid strength until they are taken out of the vagina, and the like. The filaments made of said synthetic polymers, however, do not satisfy these physical conditions. Therefore, the tampons made of such filaments are not fully suitable.

This invention is characterized by the use of the staple fibers which are obtained by spinning a lower alkyl or a lower hydroxyalkyl substituted cellulose ether as a raw material. The particular cellulose ethers may satisfy the above mentioned conditions, not only in the case of molding in the presence of absence of pressure to form a tampon.

The lower alkyl or lower hydroxyalkyl substituted cellulose ethers to be used for this invention are selected from those which have water soluble and thermogelation properties. Preferably, there may be mentioned, for example, methyl cellulose (substitution ratio of ether is from 0.8 to 1.1), ethyl cellulose (substitution ratio of ether is from 0.8 to 1.0), hydroxyethyl cellulose (substitution ratio of ether is from 1.5 to 1.7), hydroxypropyl cellulose (substitution ratio of ether is 1.8 to 2.0) and hydroxypropylmethyl cellulose (substitution ratio of ether is from 0.9 to 1.3).

Standard spinning technique may be used for the manufacture of filaments by means of spinning the cellulose ethers of this invention. Methyl cellulose, for example, may be spun by a wet spinning procedure in combination with a suitable coagulation bath when water is used as a solvent, and also by dry spinning procedure when an organic solvent having a lower boiling point is used as a solvent.

The most economical method can be carried by a melt spinning method which comprises heating to melt the raw material alone, or heating to melt the material together with plasticizer, and followed by extruding it to form a filament.

It is also possible to extrude the molten material in a form of a thin foil, and highly orient the produced film, and then split it into filaments.

The most advantageous method amongst the above described methods is the melt spinning method, thereby providing the filaments having the most excellent properties.

In order to mold the multi-filament of the cellulose ether according to this invention to form the tampon, the spun filaments may be first cut into 2 cm to 3 cm lengths. A cotton-like band is then made from the filaments along using conventional dry carding technique. Alternatively, the band is made from the mixture of the filaments and absorbent cotton, staple fibre and the like. The resulting cotton-like band or ribbon may be used not only as an absorber for the blood of menses as a sanitary pad (absorbent napkin of patch type) by cutting to the required size, but also as a tampon by compression molding with a compression molding machine. It is also possible to prepare a tampon by tightly enveloping the filaments with a water-soluble film or the like without compression.

The staple fiber obtained by the above procedures is also processed to gauze, bandages, and the like through a standard weaving process. These products are used for the absorbers of blood due to wounds and operations. Further, such staple fiber can be employed for the manufacture of lace fabrics by utilizing its water dispersibility, as in the case of the conventional water soluble fibers.

The superlative use of the water dispersible filaments according to this invention is, however, as tampons for menstrual blood. This is evident from the fact that such filaments of the ethers have excellent compression molding properties which is an important property for the manufacture of tampons, and is thus distinguished from the other synthetic water-soluble fibers. Further, it is apparent that the filaments have the most suitable properties for tampons from the following facts:

The water dispersible tampon according to this invention maintains its soft state without immediately dissolving even when it absorbed the blood of menses in the vagina, while the tampon immediately dissolves in the water when it has been discarded in a flush toilet.

If the tampon was prepared from the mixture of a filament and other fibers in the above case, the said other fiber is rapidly restored to the unbound state, whereby the tampon may be easily be flushed. It is considered for this reason, that the cellulose ethers have thermogelation properties and the cellulose ether becomes water insoluble at the higher temperatures, than the respective thermogelation temperature, wherein said thermogelation temperatures decrease gradually, in proportion to the increase in quantities of the coexisting salts. This theory is capable of explaining why when the tampon of this invention absorbs the blood of menses which has a temperature near the body temperature and contains salts but is insoluble in blood. This theory also explains why the tampon softens yet is capable of retaining its shape in the vagina, whereas when the tampon is taken out of the vagina, it is easily soluble in the flush water of a toilet, which water has a lower temperature than the body temperature, and low content of salts.

Since the cellulose ethers used in this invention also exhibit a weak property similar to a surface activity, the absorbers made by such cellulose ethers have excellent properties for the object of this invention due to the fact that they can absorb easily even though the blood of menses contains many contaminants such as the decomposition products of protein; their absorption coefficients are higher than that of the conventional absorbent cotton and the like; and the blood of menses absorbed is not releasable. Further, the absorber of the blood and the like according to this invention may be expected to recycle gradually to the natural cycle with decomposition by bacteria and enzymes after the absorbers are dispersed in water, and followed by the dissolution.

The following examples will illustrate the novel water dispersible absorber of this invention.

EXAMPLE 1

One Kg of methyl cellulose described in Japan Pharmacopoeia (average molecular weight is 41,000) was added to 5 liters of boiling water, and the mixture was well stirred. 4 liters of cold water were added to the mixture to form a suspension. The suspension was cooled in ice-water to dissolve the methyl cellulose. The resulting original solution was subjected to defoaming process. The solution was then spun with a nozzle having 100 holes with a respective diameter of 0.08 mm at 20° C, and was coagulated in an acetate bath at room temperature. Multi-filaments of methyl cellulose were thus produced.

EXAMPLE 2

One hundred grams of methyl cellulose described in Japan Pharmacopoeia (average molecular weight is 41,000) were dispersed with stirring in 700 g of ethylene dichloride. 300 G of methyl alcohol was gradually added to the dispersion to dissolve the whole. The resulting original solution was defoamed, and extruded into hot air at the temperature in the range of 100° C to 110° C by the use of a nozzle having 50 holes of the respective diameter of 0.12 mm. Methyl alcohol as solvent was vaporized. Multi-filaments of methyl cellulose were thus obtained.

EXAMPLE 3

Hydroxypropyl cellulose (average molecular weight is 240,000) was charged, in a powdery state, into a screw extruder (L/D=20) having diameter of 25 mm. Initially, the hydroxypropyl cellulose was softened at 150° C, and then kneaded at 180° C to 190° C. This kneaded material was extruded at 210° C. to spin with a nozzle of 20 holes having diameter of 0.3 mm located on the tip of the extruder at the spinning rate of 400 m/min. There were thus obtained homogeneous multi-filaments having diameter of $10\mu$ to $20\mu$.

EXAMPLE 4

The procedures described in the preceding Example 3 were repeated, except that methyl cellulose (average molecular weight is 110,000) was substituted for methyl cellulose (average molecular weight is 240,000).

EXAMPLE 5

A mixture of 95 parts by weight of hydroxypropyl cellulose (average molecular weight is 240,000) and 5 parts by weight of polypropylene glycol (molecular weight is 400) was charged into the screw used in the preceding Example 3, and softened at 140° C. The softened material was kneaded at 160° C to 170° C., and extruded to spin at 200° C at the spinning rate of 500 m/min. Homogeneous multi-filaments having the diameter of $10\mu$ to $20\mu$ were thus obtained.

EXAMPLE 6

A mixture of 90 parts by weight of methyl cellulose (average molecular weight is 41,000) and 10 parts by weight of propylene glycol is charged into the screw extruder used in the preceding Example 3, and softened at 150° C. The softened material was kneaded at 180° C to 190° C., and extruded to spin at 200° C at the spinning rate of 250 m/min. There were thus obtained homogeneous multi-filaments having the diameter of $20\mu$ to $30\mu$.

EXAMPLE 7

A mixture of 93 parts by weight of hydroxyethyl cellulose, 5 parts by weight of polypropylene glycol (molecular weight is 400), 1 part by weight of triacetylene and 1 part by weight of propylene glycol was charged into the screw extruder used in the preceding Example 3, and softened at 140° C. The resulting material is kneaded at 150° to 160° C, and extruded to spin at 190° C at the spinning rate of 350 m/min. Homogeneous multifilaments having diameter of $10\mu$ to $20\mu$ were thus obtained.

EXAMPLE 8

A mixture of 95 parts by weight of hydroxypropyl methyl cellulose (average molecular weight is 80,000) and 5 parts by weight of octanol was charged into the screw extruder used in the preceding Example 3, and heated to melt at 140° C to 200° C. The molten material was then spun at the spinning rate of 200 m/min. Homogeneous multi-filaments having the diameter of 20μ to 30μ were thus obtained.

EXAMPLE 9

The multi-filaments obtained according to the procedure described in the preceding Examples 1 to 8 were cut into 25 mm to 30 mm length with a cutter. Cotton-like rolls were made from the cuttings by means of the standard technic and apparatus for the manufacture of absorbent cotton.

The cut staples of methyl cellulose and the staples of absorbent cotton were charged into a cotton feeder in the mixing ratio of 20 to 80 with a quantitative feeder.

Said two staples were thus mixed with each other. The mixture was processed to make a cotton layer having a thickness of about 10 mm through the steps of the standard manufacture of absorbent cotton. The resulting cotton-like band was in a wide band form, which was passed through a roller press, and rolled to a cotton-like band having a width of 100.0 mm, and followed by producing a roll having suitable length.

This cotton-like band may be directly used as an absorber for blood and the like, by cutting it into a suitable length. This cotton-like band may be also used as a tampon. The tampon was made by cutting said band to a strip of 80 mm length, fitting it with a string for removal from the vagina and compressing it with a compression molding machine.

EXAMPLE 10

The procedures described in the proceding Example 9 were repeated, except that a mixture of the staples of hydroxypropyl cellulose and the staples of absorbent cotton in the ratio of 35 to 65 were substituted for the mixture of the staples of methyl cellulose and the staples of absorbent cotton in the ratio of 20 to 80.

What is claimed is:

1. A soft vaginal tampon for the absorption of menstrual blood, which comprises a filamentary material of a one to three carbon alkyl or a one to three carbon hydroxyalkyl substituted cellulose ether having thermogelation properties in water which material is substantially water soluble at room temperature yet is substantially insoluble in menstural blood at body temperature, and which maintains its softness without immediately dissolving after absorbing menstural blood in the vagina.

2. The tampon of claim 1, wherein the filamentary material is used together with a filamentary material of absorbent cotton or staple fibre.

3. The tampon of claim 1, wherein the lower alkyl or a lower hydroxyalkyl substituted cellulose ether is selected from the group consisting of methyl cellulose, ethylcellulose, hydroxyethyl cellulose, hydroxypropyl cellulose, and hydroxypropylmethyl cellulose.

4. The tampon of claim 1, wherein the lower alkyl subsituted cellulose ether is methyl cellulose.

5. The tampon of claim 1, wherein the lower alkyl substituted cellulose ether is ethyl cellulose.

6. The tampon of claim 1, wherein the lower hydroxyalkyl substituted cellulose ether is hydroxyethyl cellulose.

7. The tampon of claim 1, wherein the lower hydroxyalkyl substituted cellulose ether is hydroxypropyl cellulose.

8. The tampon of claim 1, wherein the lower hydroxyalkyl substituted cellulose ether is hydroxypropylmethyl cellulose.

* * * * *